(12) United States Patent
Stotz et al.

(10) Patent No.: US 12,233,250 B2
(45) Date of Patent: Feb. 25, 2025

(54) DEVICE FOR INDUCTIVE ENERGY TRANSMISSION INTO A HUMAN BODY AND USE THEREOF

(71) Applicant: KARDION GMBH, Stuttgart (DE)

(72) Inventors: Ingo Stotz, Ditzingen (DE); Samuel Vasconcelos Araujo, Esslingen (DE); Michael Jiptner, Besigheim (DE)

(73) Assignee: Kardion GmbH, Stuttgart (DE)

( * ) Notice: Subject to any disclaimer, the term of this patent is extended or adjusted under 35 U.S.C. 154(b) by 1092 days.

(21) Appl. No.: 17/051,414

(22) PCT Filed: May 2, 2019

(86) PCT No.: PCT/EP2019/061315
§ 371 (c)(1),
(2) Date: Aug. 30, 2021

(87) PCT Pub. No.: WO2019/211410
PCT Pub. Date: Nov. 7, 2019

(65) Prior Publication Data
US 2021/0386990 A1 Dec. 16, 2021

(30) Foreign Application Priority Data

May 2, 2018 (DE) .......................... 102018206750.3

(51) Int. Cl.
*A61M 60/871* (2021.01)
*A61M 60/148* (2021.01)
(Continued)

(52) U.S. Cl.
CPC ........ *A61M 60/148* (2021.01); *A61M 60/178* (2021.01); *A61M 60/205* (2021.01); *A61M 60/873* (2021.01)

(58) Field of Classification Search
CPC ........ A61M 2205/8243; A61M 60/178; A61M 60/216; A61M 60/422; A61M 60/538;
(Continued)

(56) References Cited

U.S. PATENT DOCUMENTS

| 2,254,698 A | 9/1941 | Hansen, Jr. |
| 3,085,407 A | 4/1963 | Tomlinson |

(Continued)

FOREIGN PATENT DOCUMENTS

| CA | 3 000 581 | 4/2017 |
| CN | 103143072 | 6/2013 |

(Continued)

OTHER PUBLICATIONS

International Search Report and Written Opinion received in PCT Application No. PCT/EP2019/061315, dated Jul. 25, 2019 in 15 pages.

(Continued)

*Primary Examiner* — Jon Eric C Morales
(74) *Attorney, Agent, or Firm* — Knobbe, Martens, Olson & Bear, LLP

(57) ABSTRACT

The invention relates to a device (10; 10*a*) for inductive energy transfer into a human body (1), having a transmitter unit (11) with a housing (12), in which at least one transmitter coil (14) is arranged, wherein the housing (12) comprises a contact surface (23), which is configured in order to be brought into surface contact with the body (1), and a receiver unit (20) that can be positioned in the body (1) with a receiver coil (21), wherein a heat-insulating element (26) and a heat-conducting element (30; 30*a*) are arranged between the transmitter coil (14) and the body.

20 Claims, 1 Drawing Sheet

(51) Int. Cl.
*A61M 60/178* (2021.01)
*A61M 60/205* (2021.01)
*A61M 60/873* (2021.01)

(58) Field of Classification Search
CPC ............... A61M 60/875; A61N 1/3787; H05K 7/20436
See application file for complete search history.

(56) References Cited

U.S. PATENT DOCUMENTS

| | | |
|---|---|---|
| 3,614,181 A | 10/1971 | Meeks |
| 3,645,268 A | 2/1972 | Capote |
| 3,747,998 A | 7/1973 | Klein et al. |
| 3,790,878 A | 2/1974 | Brokaw |
| 3,807,813 A | 4/1974 | Milligan |
| 4,441,210 A | 4/1984 | Hochmair et al. |
| 4,888,009 A | 12/1989 | Lederman et al. |
| 4,888,011 A | 12/1989 | Kung et al. |
| 4,896,754 A | 1/1990 | Carlson et al. |
| 5,000,177 A | 3/1991 | Hoffmann et al. |
| 5,195,877 A | 3/1993 | Kletschka |
| 5,289,821 A | 3/1994 | Swartz |
| 5,443,503 A | 8/1995 | Yamane |
| 5,599,173 A | 2/1997 | Chen et al. |
| 5,613,935 A | 3/1997 | Jarvik |
| 5,629,661 A | 5/1997 | Ooi et al. |
| 5,690,674 A | 11/1997 | Diaz |
| 5,702,430 A | 12/1997 | Larson, Jr. et al. |
| 5,713,954 A | 2/1998 | Rosenberg et al. |
| 5,766,207 A | 6/1998 | Potter et al. |
| 5,814,900 A | 9/1998 | Esser |
| 5,843,141 A | 12/1998 | Bischoff et al. |
| 5,888,242 A | 3/1999 | Antaki et al. |
| 6,053,873 A | 4/2000 | Govari et al. |
| 6,058,958 A | 5/2000 | Benkowski et al. |
| 6,149,405 A | 11/2000 | Abe et al. |
| 6,212,430 B1 | 4/2001 | Kung et al. |
| 6,224,540 B1 | 5/2001 | Lederman et al. |
| 6,254,359 B1 | 7/2001 | Aber |
| 6,264,601 B1 | 7/2001 | Jassawalla et al. |
| 6,324,430 B1 | 11/2001 | Zarinetchi et al. |
| 6,324,431 B1 | 11/2001 | Zarinetchi et al. |
| 6,361,292 B1 | 3/2002 | Chang et al. |
| 6,366,817 B1 | 4/2002 | Kung |
| 6,389,318 B1 | 5/2002 | Zarinetchi et al. |
| 6,398,734 B1 | 6/2002 | Cimochowski et al. |
| 6,400,991 B1 | 6/2002 | Kung |
| 6,442,434 B1 | 8/2002 | Zarinetchi et al. |
| 6,445,956 B1 | 9/2002 | Laird et al. |
| 6,471,713 B1 | 10/2002 | Vargas et al. |
| 6,496,733 B2 | 12/2002 | Zarinetchi et al. |
| 6,508,756 B1 | 1/2003 | Kung et al. |
| 6,516,227 B1 | 2/2003 | Meadows et al. |
| 6,527,698 B1 | 3/2003 | Kung et al. |
| 6,530,876 B1 | 3/2003 | Spence |
| 6,540,658 B1 | 4/2003 | Fasciano et al. |
| 6,553,263 B1 | 4/2003 | Meadows et al. |
| 6,561,975 B1 | 5/2003 | Pool et al. |
| 6,592,620 B1 | 7/2003 | Lancisi et al. |
| 6,979,338 B1 | 12/2005 | Loshakove et al. |
| 7,062,331 B2 | 6/2006 | Zarinetchi et al. |
| 7,070,398 B2 | 7/2006 | Olsen et al. |
| 7,155,291 B2 | 12/2006 | Zarinetchi et al. |
| 7,160,243 B2 | 1/2007 | Medvedev |
| 7,338,521 B2 | 3/2008 | Antaki et al. |
| 7,513,864 B2 | 4/2009 | Kantrowitz et al. |
| 7,520,850 B2 | 4/2009 | Brockway |
| 7,762,941 B2 | 7/2010 | Jarvik |
| 7,794,384 B2 | 9/2010 | Sugiura et al. |
| 7,819,916 B2 | 10/2010 | Yaegashi |
| 7,942,805 B2 | 5/2011 | Shambaugh, Jr. |
| 7,959,551 B2 | 6/2011 | Jarvik |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,231,519 B2 | 7/2012 | Reichenbach et al. |
| 8,489,200 B2 | 7/2013 | Zarinetchi et al. |
| 8,608,635 B2 | 12/2013 | Yomtov et al. |
| 8,612,002 B2 | 12/2013 | Faltys et al. |
| 8,620,447 B2 | 12/2013 | D'Ambrosio et al. |
| 8,766,788 B2 | 7/2014 | D'Ambrosio |
| 8,827,890 B2 | 9/2014 | Lee et al. |
| 8,862,232 B2 | 10/2014 | Zarinetchi et al. |
| 8,870,739 B2 | 10/2014 | LaRose et al. |
| 8,900,114 B2 | 12/2014 | Tansley et al. |
| 8,961,389 B2 | 2/2015 | Zilbershlag |
| 9,002,468 B2 | 4/2015 | Shea et al. |
| 9,002,469 B2 | 4/2015 | D'Ambrosio |
| 9,071,182 B2 | 6/2015 | Yoshida et al. |
| 9,220,826 B2 | 12/2015 | D'Ambrosio |
| 9,283,314 B2 | 3/2016 | Prasad et al. |
| 9,381,286 B2 | 7/2016 | Spence et al. |
| 9,440,013 B2 | 9/2016 | Dowling et al. |
| 9,456,898 B2 | 10/2016 | Barnes et al. |
| 9,486,566 B2 | 11/2016 | Siess |
| 9,492,600 B2 | 11/2016 | Strueber et al. |
| 9,539,094 B2 | 1/2017 | Dale et al. |
| 9,561,362 B2 | 2/2017 | Malinowski |
| 9,569,985 B2 | 2/2017 | Alkhatib et al. |
| 9,592,397 B2 | 3/2017 | Hansen et al. |
| 9,603,984 B2 | 3/2017 | Romero et al. |
| 9,616,107 B2 | 4/2017 | VanAntwerp et al. |
| 9,713,701 B2 | 7/2017 | Sarkar et al. |
| 9,717,831 B2 | 8/2017 | Schuermann |
| 9,724,083 B2 | 8/2017 | Quadri et al. |
| 9,800,172 B1 | 10/2017 | Leabman |
| 9,833,314 B2 | 12/2017 | Corbett |
| 9,833,611 B2 | 12/2017 | Govea et al. |
| 9,848,899 B2 | 12/2017 | Sliwa et al. |
| 9,974,894 B2 | 5/2018 | Morello |
| 10,143,571 B2 | 12/2018 | Spence et al. |
| 10,463,508 B2 | 11/2019 | Spence et al. |
| 10,732,583 B2 | 8/2020 | Rudser |
| 10,944,293 B2 | 3/2021 | Nakao |
| 11,000,282 B2 | 5/2021 | Schuelke et al. |
| 11,056,878 B2 | 7/2021 | Gao et al. |
| 11,065,437 B2 | 7/2021 | Aber et al. |
| 11,103,715 B2 | 8/2021 | Fort |
| 11,110,265 B2 | 9/2021 | Johnson |
| 11,179,559 B2 | 11/2021 | Hansen |
| 11,224,737 B2 | 1/2022 | Petersen et al. |
| 11,291,826 B2 | 4/2022 | Tuval et al. |
| 11,316,371 B1 | 4/2022 | Partovi et al. |
| 11,317,988 B2 | 5/2022 | Hansen et al. |
| 11,344,717 B2 | 5/2022 | Kallenbach et al. |
| 11,351,359 B2 | 6/2022 | Clifton et al. |
| 11,351,360 B2 | 6/2022 | Rudser et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,389,641 B2 | 7/2022 | Nguyen et al. |
| 11,406,483 B2 | 8/2022 | Wirbisky et al. |
| 11,406,520 B2 | 8/2022 | Lam |
| 11,406,802 B2 | 8/2022 | DeGraaf et al. |
| 11,413,443 B2 | 8/2022 | Hodges et al. |
| 11,413,444 B2 | 8/2022 | Nix et al. |
| 11,439,806 B2 | 9/2022 | Kimball et al. |
| 11,471,692 B2 | 10/2022 | Aghassian et al. |
| 11,497,906 B2 | 11/2022 | Grace et al. |
| 11,517,737 B2 | 12/2022 | Struthers et al. |
| 11,517,738 B2 | 12/2022 | Wisniewski |
| 11,517,740 B2 | 12/2022 | Agarwa et al. |
| 11,529,508 B2 | 12/2022 | Jablonsk et al. |
| 11,583,671 B2 | 2/2023 | Nguyen et al. |
| 11,596,727 B2 | 3/2023 | Siess et al. |
| 11,602,624 B2 | 3/2023 | Siess et al. |
| 11,682,924 B2 | 6/2023 | Hansen et al. |
| 11,689,057 B2 | 6/2023 | Hansen |
| 11,699,551 B2 | 7/2023 | Diekhans et al. |
| 11,745,005 B2 | 9/2023 | Delgado, III |
| 11,752,354 B2 | 9/2023 | Stotz et al. |
| 11,804,767 B2 | 10/2023 | Vogt et al. |
| 11,881,721 B2 | 1/2024 | Araujo et al. |

(56) References Cited

U.S. PATENT DOCUMENTS

| | | |
|---|---|---|
| 11,996,699 B2 | 5/2024 | Vasconcelos Araujo et al. |
| 2001/0016686 A1 | 8/2001 | Okada et al. |
| 2002/0177324 A1 | 11/2002 | Metzler |
| 2003/0040765 A1 | 2/2003 | Breznock |
| 2003/0125766 A1 | 7/2003 | Ding |
| 2003/0130581 A1 | 7/2003 | Salo et al. |
| 2004/0167410 A1 | 8/2004 | Hettrick |
| 2005/0006083 A1* | 1/2005 | Chen .................. H01L 23/36 257/E23.101 |
| 2005/0107658 A1 | 5/2005 | Brockway |
| 2005/0107847 A1 | 5/2005 | Gruber et al. |
| 2006/0004423 A1 | 1/2006 | Boveja et al. |
| 2006/0190036 A1 | 8/2006 | Wendel et al. |
| 2006/0196277 A1 | 9/2006 | Allen et al. |
| 2007/0129767 A1 | 6/2007 | Wahlstrand |
| 2007/0282209 A1 | 12/2007 | Lui et al. |
| 2008/0015481 A1 | 1/2008 | Bergin et al. |
| 2008/0079392 A1 | 4/2008 | Baarman et al. |
| 2008/0082005 A1 | 4/2008 | Stern et al. |
| 2008/0211455 A1 | 9/2008 | Park et al. |
| 2008/0266922 A1 | 10/2008 | Mumtaz et al. |
| 2009/0010462 A1 | 1/2009 | Ekchian et al. |
| 2009/0024042 A1 | 1/2009 | Nunez et al. |
| 2009/0134711 A1 | 5/2009 | Issa et al. |
| 2009/0198307 A1 | 8/2009 | Mi et al. |
| 2009/0198312 A1 | 8/2009 | Barker |
| 2009/0276016 A1 | 11/2009 | Phillips et al. |
| 2009/0312650 A1 | 12/2009 | Maile et al. |
| 2010/0010582 A1 | 1/2010 | Carbunaru |
| 2010/0191035 A1 | 7/2010 | Kang et al. |
| 2010/0219967 A1 | 9/2010 | Kaufmann |
| 2010/0280568 A1 | 11/2010 | Bulkes et al. |
| 2010/0312310 A1 | 12/2010 | Meskens |
| 2010/0331918 A1 | 12/2010 | Digiore et al. |
| 2010/0331920 A1 | 12/2010 | Digiore et al. |
| 2011/0071336 A1 | 3/2011 | Yomtov |
| 2011/0137394 A1 | 6/2011 | Lunsford et al. |
| 2011/0224720 A1 | 9/2011 | Kassab et al. |
| 2012/0019201 A1 | 1/2012 | Peterson |
| 2012/0022645 A1 | 1/2012 | Burke |
| 2012/0050931 A1 | 3/2012 | Terry et al. |
| 2012/0112543 A1 | 5/2012 | van Wageningen et al. |
| 2012/0158074 A1 | 6/2012 | Hall |
| 2012/0212178 A1 | 8/2012 | Kim |
| 2012/0235633 A1 | 9/2012 | Kesler et al. |
| 2013/0069651 A1 | 3/2013 | Lumiani |
| 2013/0099585 A1 | 4/2013 | Von Novak et al. |
| 2013/0116575 A1 | 5/2013 | Mickle et al. |
| 2013/0303970 A1 | 11/2013 | Keenan et al. |
| 2014/0012282 A1 | 1/2014 | Fritsch |
| 2014/0039587 A1 | 2/2014 | Romero |
| 2014/0063666 A1 | 3/2014 | Kallal et al. |
| 2014/0094645 A1 | 4/2014 | Lafontaine et al. |
| 2014/0104898 A1 | 4/2014 | Yeo et al. |
| 2014/0107754 A1 | 4/2014 | Fuhs et al. |
| 2014/0135884 A1 | 5/2014 | Tockman et al. |
| 2014/0194058 A1 | 7/2014 | Lee et al. |
| 2014/0233184 A1 | 8/2014 | Thompson et al. |
| 2014/0249603 A1 | 9/2014 | Yan et al. |
| 2014/0265620 A1 | 9/2014 | Hoarau et al. |
| 2015/0008755 A1 | 1/2015 | Sone |
| 2015/0028805 A1 | 1/2015 | Dearden et al. |
| 2015/0090372 A1 | 4/2015 | Branagan et al. |
| 2015/0196076 A1 | 7/2015 | Billingslea |
| 2015/0290372 A1 | 10/2015 | Muller et al. |
| 2015/0290373 A1* | 10/2015 | Rudser ................ A61M 60/538 623/3.27 |
| 2015/0333532 A1 | 11/2015 | Han et al. |
| 2015/0380972 A1 | 12/2015 | Fort |
| 2016/0022889 A1 | 1/2016 | Bluvshtein et al. |
| 2016/0067395 A1 | 3/2016 | Jimenez et al. |
| 2016/0081680 A1 | 3/2016 | Taylor |
| 2016/0087558 A1 | 3/2016 | Yamamoto |
| 2016/0095968 A1 | 4/2016 | Rudser |
| 2016/0175501 A1 | 6/2016 | Schuermann |
| 2016/0268846 A1 | 9/2016 | Akuzawa et al. |
| 2016/0271309 A1 | 9/2016 | Throckmorton et al. |
| 2016/0331980 A1 | 11/2016 | Strommer et al. |
| 2016/0344302 A1 | 11/2016 | Inoue |
| 2017/0047781 A1 | 2/2017 | Stanislawski et al. |
| 2017/0070082 A1 | 3/2017 | Zheng et al. |
| 2017/0136164 A1 | 5/2017 | Yeatts |
| 2017/0143977 A1 | 5/2017 | Kaib et al. |
| 2017/0202575 A1 | 7/2017 | Stanfield et al. |
| 2017/0203104 A1 | 7/2017 | Nageri et al. |
| 2017/0231717 A1 | 8/2017 | Forsell |
| 2017/0271919 A1 | 9/2017 | Von Novak, III et al. |
| 2017/0275799 A1 | 9/2017 | Chen |
| 2017/0288448 A1 | 10/2017 | Kranz et al. |
| 2017/0303375 A1 | 10/2017 | Woodhead |
| 2017/0353053 A1 | 12/2017 | Muratov |
| 2017/0354812 A1 | 12/2017 | Callaghan et al. |
| 2018/0078329 A1 | 3/2018 | Hansen et al. |
| 2018/0194236 A1 | 7/2018 | Elshaer et al. |
| 2018/0207336 A1 | 7/2018 | Solem |
| 2018/0256796 A1 | 9/2018 | Hansen |
| 2018/0256800 A1 | 9/2018 | Conyers et al. |
| 2018/0280708 A1 | 10/2018 | Escalona et al. |
| 2018/0287405 A1 | 10/2018 | Govindaraj |
| 2018/0316209 A1 | 11/2018 | Gliner |
| 2019/0004037 A1 | 1/2019 | Zhang et al. |
| 2019/0060543 A1 | 2/2019 | Khanal et al. |
| 2019/0068004 A1 | 2/2019 | Louis |
| 2019/0097447 A1 | 3/2019 | Partovi |
| 2019/0175808 A1 | 6/2019 | Zilbershlag et al. |
| 2019/0222064 A1 | 7/2019 | Du et al. |
| 2019/0344000 A1 | 11/2019 | Kushwaha et al. |
| 2019/0351120 A1 | 11/2019 | Kushwaha et al. |
| 2019/0393735 A1 | 12/2019 | Lee et al. |
| 2020/0054806 A1 | 2/2020 | Sun |
| 2020/0139032 A1 | 5/2020 | Bryson et al. |
| 2020/0227954 A1 | 7/2020 | Ding et al. |
| 2020/0350812 A1 | 11/2020 | Vogt et al. |
| 2021/0052793 A1 | 2/2021 | Struthers et al. |
| 2021/0057804 A1 | 2/2021 | Wenning |
| 2021/0143688 A1 | 5/2021 | Agrawal et al. |
| 2021/0290931 A1 | 9/2021 | Baumbach |
| 2021/0322011 A1 | 10/2021 | Schuelke et al. |
| 2021/0336484 A1 | 10/2021 | Araujo et al. |
| 2021/0379360 A1 | 12/2021 | Schellenberg |
| 2021/0393944 A1 | 12/2021 | Wenning |
| 2022/0080184 A1 | 3/2022 | Clifton et al. |
| 2022/0080185 A1 | 3/2022 | Clifton et al. |
| 2022/0320901 A1 | 10/2022 | Araujo et al. |
| 2023/0191141 A1 | 6/2023 | Wenning et al. |
| 2023/0352236 A1 | 11/2023 | Diekhans et al. |
| 2023/0381526 A1 | 11/2023 | Stotz et al. |

FOREIGN PATENT DOCUMENTS

| | | |
|---|---|---|
| CN | 103942511 | 7/2014 |
| CN | 104274873 | 1/2015 |
| CN | 104888293 | 3/2017 |
| CN | 106776441 | 5/2017 |
| DE | 103 02 550 | 8/2004 |
| DE | 10 2012 200 912 | 7/2013 |
| DE | 11 2012 005 944 | 12/2014 |
| DE | 10 2016 106 683 | 10/2016 |
| DE | 10 2017 213 475 | 2/2019 |
| DE | 10 2018 204 604 | 10/2019 |
| DE | 10 2018 204 610 | 10/2019 |
| DE | 10 2018 206 714 | 11/2019 |
| DE | 10 2018 206 724 | 11/2019 |
| DE | 10 2018 206 725 | 11/2019 |
| DE | 10 2018 206 727 | 11/2019 |
| DE | 10 2018 206 731 | 11/2019 |
| DE | 10 2018 206 750 | 11/2019 |
| DE | 10 2018 206 754 | 11/2019 |
| DE | 10 2018 206 758 | 11/2019 |
| DE | 10 2018 222 505 | 6/2020 |
| EP | 0 930 086 | 7/1999 |
| EP | 2 752 209 | 7/2014 |
| EP | 2 782 210 | 9/2014 |
| EP | 2 859 911 | 4/2015 |

(56) References Cited

FOREIGN PATENT DOCUMENTS

| | | |
|---|---|---|
| EP | 2 966 753 | 1/2016 |
| EP | 2 454 799 | 9/2016 |
| EP | 2 709 689 | 4/2017 |
| EP | 3 220 505 | 9/2017 |
| EP | 3 357 523 | 1/2021 |
| EP | 3 423 126 | 2/2021 |
| EP | 3 490 628 | 2/2021 |
| EP | 3 198 677 | 3/2021 |
| EP | 3 248 647 | 3/2021 |
| EP | 3 436 106 | 3/2021 |
| EP | 3 509 661 | 3/2021 |
| EP | 3 528 863 | 3/2021 |
| EP | 3 436 105 | 4/2021 |
| EP | 3 116 407 | 5/2021 |
| EP | 3 131 600 | 6/2021 |
| EP | 3 827 876 | 6/2021 |
| EP | 2 608 731 | 7/2021 |
| EP | 2 599 510 | 10/2021 |
| EP | 3 077 018 | 10/2021 |
| EP | 3 485 936 | 10/2021 |
| EP | 3 539 613 | 2/2022 |
| EP | 2 858 718 | 3/2022 |
| EP | 3 624 867 | 3/2022 |
| EP | 3 755 237 | 4/2022 |
| EP | 3 497 775 | 7/2022 |
| EP | 3 711 788 | 8/2022 |
| EP | 2 654 883 | 9/2022 |
| EP | 3 485 819 | 9/2022 |
| EP | 3 600 477 | 10/2022 |
| EP | 3 808 408 | 11/2022 |
| EP | 3 858 422 | 11/2022 |
| EP | 2 892 583 | 1/2023 |
| EP | 3 597 231 | 1/2023 |
| EP | 3 856 275 | 1/2023 |
| EP | 3 003 420 | 2/2023 |
| EP | 3 946 511 | 4/2023 |
| EP | 3 826 104 | 5/2023 |
| JP | H11-178249 | 7/1999 |
| JP | 2013-013216 | 1/2013 |
| JP | 2018-046708 | 3/2018 |
| KR | 10-1185112 | 9/2012 |
| WO | WO 2008/106103 | 9/2008 |
| WO | WO 2009/023905 | 2/2009 |
| WO | WO 2009/029977 | 3/2009 |
| WO | WO 2010/042054 | 4/2010 |
| WO | WO 2011/007300 | 1/2011 |
| WO | WO 2012/147061 | 11/2012 |
| WO | WO 2013/164831 | 11/2013 |
| WO | WO 2015/152732 | 10/2015 |
| WO | WO 2017/021846 | 2/2017 |
| WO | WO 2017/060257 | 4/2017 |
| WO | WO 2017/066257 | 4/2017 |
| WO | WO 2017/089440 | 6/2017 |
| WO | WO 2017/118738 | 7/2017 |
| WO | WO 2017/165372 | 9/2017 |
| WO | WO 2017/218349 | 12/2017 |
| WO | WO 2018/033799 | 2/2018 |
| WO | WO 2018/100192 | 6/2018 |
| WO | WO 2019/025258 | 2/2019 |
| WO | WO 2019/025259 | 2/2019 |
| WO | WO 2019/025260 | 2/2019 |
| WO | WO 2019/101786 | 5/2019 |
| WO | WO 2019/145253 | 8/2019 |
| WO | WO 2019/158996 | 8/2019 |
| WO | WO 2019/183247 | 9/2019 |
| WO | WO 2019/185511 | 10/2019 |
| WO | WO 2019/185512 | 10/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/229224 | 12/2019 |
| WO | WO 2019/234151 | 12/2019 |
| WO | WO 2019/241556 | 12/2019 |
| WO | WO 2019/244031 | 12/2019 |
| WO | WO 2020/089429 | 5/2020 |
| WO | WO 2023/076869 | 5/2023 |

OTHER PUBLICATIONS

International Preliminary Report on Patentability and Written Opinion received in PCT/EP2019/061315, dated Nov. 12, 2020 in 8 pages.
Atkinson et al., "Pulse-Doppler Ultrasound and Its Clinical Application", The Yale Journal of Biology and Medicine, 1977, vol. 50, pp. 367-373.
Leguy et al., "Assessment of Blood vol. Flow in Slightly Curved Arteries from a Single Velocity Profile", Journal of Biomechanics, 2009, pp. 1664-1672.
Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.
Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.
Vieli, A., "Doppler Flow Determination", BJA: British Journal of Anaesthesia, 1988, vol. 60, pp. 107S-112S.

* cited by examiner

DEVICE FOR INDUCTIVE ENERGY TRANSMISSION INTO A HUMAN BODY AND USE THEREOF

BACKGROUND

Field

The invention relates to a device for inductive energy transfer into a human body having a transmitter unit comprising a housing in which at least one transmitter coil is arranged, wherein the housing comprises a contact surface which is designed to be arranged at least indirectly in surface contact with the body, and a receiver unit comprising a receiver coil, which can be positioned in the body. The invention further relates to the use of a device according to the invention.

Description of the Related Art

Various devices for inductive energy transfer are known from the prior art, by means of which batteries can be charged. For example, the inductive charging of the battery of a smartphone in a corresponding charging device is known, in which an energy transfer between a transmitter coil in the charging device and a receiver coil within the mobile phone is provided. Such inductive charging processes are further also known from automotive technology in the contactless charging of a drive battery serving the drive of a vehicle.

It is further known from medical technology to implant devices into a human body that are operated by means of a battery. A device of this genre is known from DE 10 2016 106 683 A1. The known device is part of a so-called VAD (Ventricular Assist Device) system, which comprises a pump serving to support the heart of a patient. Because the energy requirement of such a pump is relatively high, it is usually necessary for the patient to constantly wear the transmitter unit for the energy transfer. In addition to a desired high level of wearing comfort, there is also the problem, in particular in case of high energy transfer rates, that the human tissue, skin, etc. located between the transmitter coil and the receiver coil is heated by the heat/thermal loss generated by the transmitter and receiver unit. For this reason, there are, for example, specifications stipulated in the framework of standards that, for example, allow for a heating of the tissue surrounding the device by a maximum of two Kelvin (ISO 14708-1; 17.1).

SUMMARY

Proceeding from the foregoing, the invention is based upon the task of further improving the devices for inductive energy transfer through the skin known in the prior art and reducing a thermal stress on the skin or tissue. The device according to the invention for inductive energy transfer into a human body having the features disclosed herein has the advantage that the thermal load of the human tissue or the skin of the patient between the receiver unit arranged in the body and the transmitter unit arranged in surface contact with the body is reduced. This makes it possible to enable relatively high energy transfer rates in the direction of the receiver unit. When implementing or using systems having relatively large performances (for example within the scope of a VAD system), in particular, this has the advantage that a relatively short charging time can be achieved, so that an increased flexibility is enabled with regard to a possibly reduced wearing time of the transmitter unit on the body of the patient.

According to the invention, in particular to the teaching of disclosed herein, it is provided that a heat-insulating element is arranged between the transmitter coil and the contact surface of the housing to the body of the patient, in the region of which the transmitter coil is arranged, said element comprising a poorer thermal conductivity than the base material of the housing or its wall section in the region of the contact surface, and a heat-conducting element is arranged on the outside of the housing on the side of the heat-insulating element facing away from the transmitter coil, wherein the heat-conducting element consists of a material having a thermal conductivity of 1 W/mK or greater.

The combination according to the invention of a heat-insulating element on the side of the housing of the device and a heat-conducting element arranged in contact with the human body has two effects: On the one hand, the heat introduction of the housing of the transmitter unit due to the self-heating of the transmitter unit into the human body is reduced in that the heat-insulating element makes the heat transfer in the direction of the skin or the tissue of the human body more difficult or reduces it. On the other hand, a heat conduction path is provided from the heated human tissue to the environment, which reduces the warming of the human tissue and avoids a heat build-up.

Advantageous further developments of the device for inductive energy transfer into a human body according to the invention are presented herein.

A first preferred structural embodiment of the device provides that the heat-insulating element is designed in the form of a heat-insulating film, preferably on the basis of an aerogel. The use of such a heat-insulating film with a relatively low thickness and high flexibility has the particular advantage that it allows a simple, space-saving arrangement in the housing.

One structural embodiment provides that the heat-insulating element is designed as an element separate from the housing and is arranged on an inner surface of the housing. As a result, different materials that are respectively optimized for the heat-insulating element as well as for the material of the housing can be used.

Alternatively, it is also conceivable for the heat-insulating element to be designed in the form of a multi-layered textile comprising preferably woven fine structures. Such a textile structure has the particular advantage that heat transfer from the housing into the body is made more difficult. Further, such an embodiment in the form of a textile has the advantage that it allows a particularly good integration of the device or the housing into a wearing device. Overall, due to the heat-insulating element, heat is mainly released in the direction of the environment away from the body, which leads to a relief of the (human) tissue.

A first constructive arrangement/embodiment of the heat-conducting element provides that the heat-conducting element abuts against the housing outside of the contact surface to the body, so that the heat-conducting element engages into operative connection with the ambient air there. In practice, this is achieved by the fact that, for example, the heat-conducting element is arranged on the housing not only in the direct region of the contact surface to the human body, but rather, for example, on regions of the housing that are spaced apart or protruding from the human body, for example in the region of free side walls of the housing.

In order to achieve an effective and cost-effective manufacture of the housing of the transmitter unit, it is advantageously provided that the housing is designed as an injection molded part made of plastic, and the heat-conducting element is designed as an insert part into a molding tool, so that the plastic is molded onto the heat-conducting element as a base or wall material of the housing.

It can further be provided that the heat-conducting element is spaced apart from the housing outside of the contact surface, and the heat-conducting element is designed flexibly so that the heat-conducting element can cling to the body. A heat dissipation surface to the environment outside of the overlapping region between the body and the housing is thereby achieved, which ensures improved heat dissipation.

Ceramic-filled polyurethanes can be provided as a possible material for the heat-conducting element.

In order to avoid additional losses due to magnetic induction, it is further provided that the heat-conducting element consists of a non-metallic and non-electrically conductive material and has a permeability number of less than 100.

Lastly, the invention also comprises the use of a device for energy transfer into a human body according to the invention as described thus far, in particular as a component of a VAD system.

Further advantages, features, and details of the invention can be found in the following description of preferred embodiments and with reference to the drawing.

BRIEF DESCRIPTION OF THE DRAWINGS

The following are shown.

DETAILED DESCRIPTION

Figure 1:
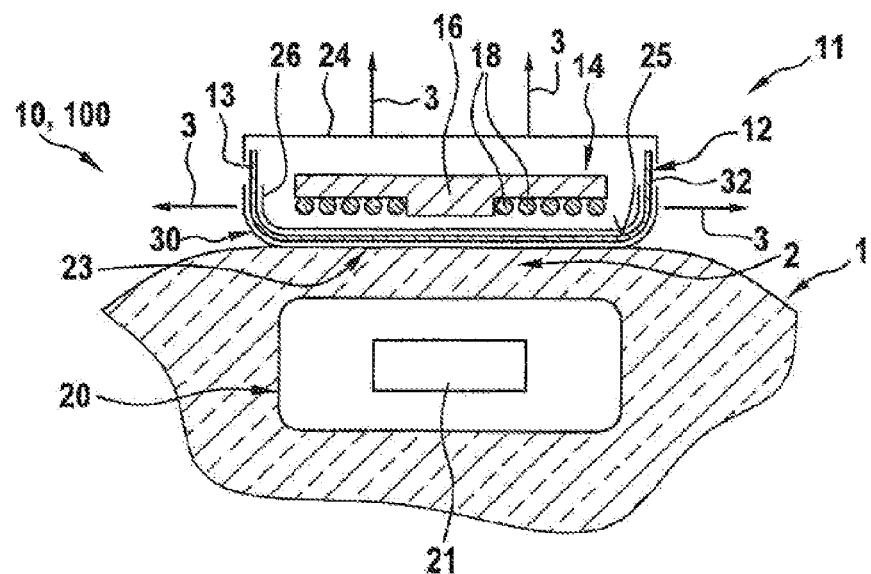
FIG. 1 a simplified schematic illustration of a device according to the invention for inductive energy transfer in a first structural design of a heat-conducting element, in which it is completely arranged in the region of a housing of the device, and FIG. 2 a view similar to that of FIG. 1, in which the heat-conducting element projects over the housing of the device laterally and is arranged in surface contact with a human body.

The same element(s) having the same function are given the same reference numerals in the figures.

FIG. 1 shows a first device 10 for inductive energy transfer into a human body 1 in a highly simplified manner. The device 10 is, in particular, a component of a VAD system 100 not shown, which is used to drive a pump supporting the heart function of a patient by means of a battery. The battery not shown in FIG. 1 is charged by means of the device 10. The battery can be either a part of the device 10 or arranged locally separated from the device, for example near the heart.

The device 10 comprises a transmitter unit 11 with a housing 12, preferably made of plastic and embodied as an injection molded part, typically consisting of multiple parts. In the interior of the housing 12, which comprises a cup-shaped base body 13, a simplified transmitter coil 14 consisting of a disk-shaped magnetic core 16 and wire windings 18 is arranged, among other things. Of course, further components are arranged within the housing 12, but these are not shown for the sake of simplicity.

The transmitter coil 14 cooperates with a receiver unit 20 arranged within the body 1, said receiver unit being implanted in the body 1. The receiver unit 20 comprises, inter alia, a receiver coil 21, which is only symbolically shown and in which energy is induced by means of the transmitter coil 14 in order to charge the battery.

The transmitter unit 11 and the housing 12 comprise a contact surface or a contact region 23, respectively, in which the housing 12 is arranged at least indirectly in contact with the body 1 of the patient, wherein human tissue 2 or skin is located between the receiver unit 20 and the transmitter unit 11.

The housing 12 of the transmitter unit 11 is closed by a housing cover 24 preferably consisting of a highly heat-conducting material in order to improve the heat generated by the self-heating of the transmitter unit 11 through heat dissipation to the environment, which is clarified by the arrows 3. Further, by way of example, a heat-insulating element 26 is arranged between the transmitter coil 14 and the contact region 23 on an inner surface 25 of the housing 12. The heat-insulating element 26 is preferably configured in the form of a heat-insulating film, particularly preferably on the basis of an aerogel. It is arranged on the side facing the contact region 23 in complete overlap with the transmitter coil 14 and, for example, projects laterally into side wall regions of the housing 12. It is provided in particular that the material of the heat-insulating element 26 has a poorer thermal conductivity than the base or wall material of the housing 12 consisting of plastic.

In addition, a heat-conducting element 30 is arranged between the housing 12 and the body 1 on the outer side of the housing 12. The heat-conducting element 30, which is in direct surface contact with the body 1 in the contact region 23, consists of a material having a thermal conductivity of greater than 1 W/mK. The heat-conducting element 30 serves to dissipate heat from the body 1 that is generated in the body 1 or the tissue 2 during the inductive charging process. For this purpose, it is provided in the device 10 that the heat-conducting element 30, which consists, for example, of a ceramic-filled polyurethane, laterally projects over the regions in which it is in direct surface contact with the body 1. Specifically, it is provided that the heat-conducting element 30 is guided outside to side walls 32 of the housing 12 projecting from the body. From there, a direct heat transfer or convection to the ambient air is possible, which is also clarified by the arrows 3. In addition, through modifications (not shown) of the element 30, its surface can be enlarged, which improves the convection to the ambient air.

Figure 2:
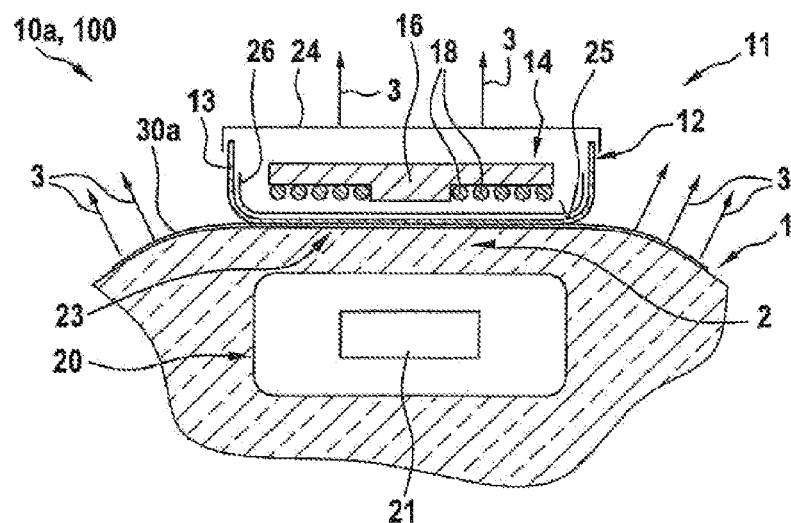

The device 10a shown in FIG. 2 differs from the device 10 in that a heat-conducting element 30a is used, which projects laterally over the contact region 23 or the housing 12 and is arranged in direct surface contact with the body 1 or clings to the body 1. As a result, a direct heat transfer and convection from the tissue 2 outside of the contact region 23 of the housing 12 to the ambient air is possible.

The device 10, 10a as described thus far can be changed or modified in many ways without departing from the idea of the invention.

In summary, the following is reiterated: The invention relates to a device (10; 10a) for inductive energy transfer into a human body (1), having a transmitter unit (11) with a housing (12), in which at least one transmitter coil (14) is arranged, wherein the housing (12) comprises a contact surface (23), which is configured in order to be brought into surface contact with the body (1), and a receiver unit (20) that can be positioned in the body (1) with a receiver coil (21), wherein a heat-insulating element (26) and a heat-conducting element (30; 30a) are arranged between the transmitter coil (14) and the body.

The invention claimed is:

1. An apparatus for inductive energy transmission, the apparatus comprising:
   a transmitter unit comprising:
   a housing comprising a contact surface configured to contact a body of a patient;
   at least one transmitter coil positioned within the housing;
   an insulating element configured to be arranged between the at least one transmitter coil and the contact surface, wherein the insulating element is configured to have a poorer thermal conductivity than a base of the housing; and
   a conductive element configured to be arranged on an outer side of the housing at least partially between the contact surface and the body of the patient on a side of the insulating element opposite from the at least one transmitter coil, the conductive element comprising a material having a thermal conductivity of 1 W/mK or greater; and
   a receiver unit configured to be positioned in the body of the patient and comprising a receiver coil.

2. The apparatus of claim 1, wherein the insulating element comprises a heat-insulating film.

3. The apparatus of claim 2, wherein the insulating element comprises a film of aerogel.

4. The apparatus of claim 1, wherein the insulating element is configured to be separate from the housing and is arranged on an inner surface of the housing.

5. The apparatus of claim 1, wherein the insulating element comprises a multi-layered textile comprising fine woven structures.

6. The apparatus of claim 1, wherein the conductive element is configured to be arranged outside of the contact surface on the housing separate from the body of the patient.

7. The apparatus of claim 6, wherein the conductive element extends along sidewalls of the housing in a direction away from the body of the patient.

8. The apparatus of claim 1, wherein the housing is configured to be injection-molded and made out of plastic, and wherein the conductive element is configured to be inserted into a molding tool, such that the plastic is molded onto the conductive element as the base of the housing.

9. The apparatus of claim 1, wherein the conductive element is configured to be positioned on the body of the patient, separate from the housing.

10. The apparatus of claim 1, wherein the conductive element is configured to be flexible and configured to cling to an outer contour of the body of the patient.

11. The apparatus of claim 1, wherein the conductive element comprises ceramic-filled polyurethane.

12. The apparatus of claim 1, wherein the conductive element comprises a non-metallic material and a non-electrically conductive material, and wherein the conductive element has a permeability of less than 100.

13. The apparatus of claim 1, wherein the insulating element extends upwards along sidewall regions of the housing and completely overlaps the at least one transmitter coil.

14. A cardiac assist system comprising:
   a cardiac assist device comprising a pump configured to assist blood flow through a heart of a patient; and
   an inductive energy transmission apparatus comprising:
   a receiver unit configured to be positioned in a body of the patient and comprising a receiver coil;
   a transmitter unit comprising:
   a housing comprising at least one transmitter coil;
   a contact surface configured to contact the body of the patient;
   an insulating element configured to have a poorer thermal conductivity than a base of the housing; and
   a conductive element configured to be positioned at least partially between the body of the patient and the contact surface of the transmitter unit on a side of the insulating element opposite from the at least one transmitter coil, the conductive element comprising a material having a thermal conductivity of 1 W/mK or greater.

15. The cardiac assist system of claim 14, wherein the insulating element is configured to be separate from the housing and is arranged on an inner surface of the housing.

16. The cardiac assist system of claim 14, wherein the insulating element extends upwards along sidewall regions of the housing and completely overlaps the at least one transmitter coil.

17. The cardiac assist system of claim 14, wherein the insulating element is a multi-layered textile comprising fine woven structures.

18. The cardiac assist system of claim 17, wherein the conductive element extends along sidewalls of the housing in a direction away from the body of the patient.

19. The cardiac assist system of claim 14, wherein the conductive element is configured to be arranged outside of the contact surface on the housing separate from the body of the patient.

20. The cardiac assist system of claim 14, wherein the conductive element is configured to be positioned on the body of the patient, separate from the housing.

* * * * *